US00PP24654P3

(12) United States Plant Patent
Olesen

(10) Patent No.: US PP24,654 P3
(45) Date of Patent: Jul. 22, 2014

(54) HYBRID TEA ROSE PLANT NAMED 'POULPMT008'

(50) Latin Name: ***Rosa* hybrid**
Varietal Denomination: Poulpmt008

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 91 days.

(21) Appl. No.: 13/507,005

(22) Filed: May 31, 2012

(65) Prior Publication Data

US 2013/0326753 P1 Dec. 5, 2013

(51) Int. Cl.
*A01H 5/00* (2006.01)

(52) U.S. Cl.
USPC ..... Plt./134; Plt./101

(58) Field of Classification Search
USPC ..... Plt./101, 130, 134
See application file for complete search history.

*Primary Examiner* — Susan McCormick Ewoldt

(57) ABSTRACT

A new garden rose plant of the Hybrid Tea class which has abundant, yellow-orange flowers and attractive foliage. This new and distinct variety has shown to be uniform and stable in the resulting generations from asexual propagation.

3 Drawing Sheets

Botanical designation: *Rosa* hybrid.
Variety denomination: 'Poulpmt008'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2004 and the resulting seeds were planted in a controlled environment in Fredensborg, Denmark. The new variety, named 'Poulpmt008', originated as a single seedling from the stated cross.

The new variety may be distinguished from its male pollen parent and female seed parent primarily by flower coloration and growth habit.

The objective of the hybridization of this rose variety was to create a new and distinct variety for garden use with unique qualities, such as:

1. Uniform and abundant yellow-orange flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpmt008' from all other varieties of which we are aware.

As part of the rose development program, Mogens N. Olesen germinated the seeds from the aforementioned hybridization during winter of 2004 and conducted evaluations on the resulting seedlings in a controlled environment in Fredensborg, Denmark. 'Poulpmt008' was selected in the spring of 2005 by the inventor as a single plant from the progeny of the aforementioned hybridization.

Asexual reproduction of 'Poulpmt008' by traditional budding and rooted cuttings was first done by Mogens N. Olesen in the nursery in Fredensborg, Denmark in July, 2005. This initial and other subsequent asexual propagations conducted in controlled environments have demonstrated that the characteristics of 'Poulpmt008' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, on 2 year old plants of 'Poulpmt008'.

Specifically illustrated in FIG. 1 are open flowers, detached flower petals, sepals detached, and the receptacle.

Figure 1:
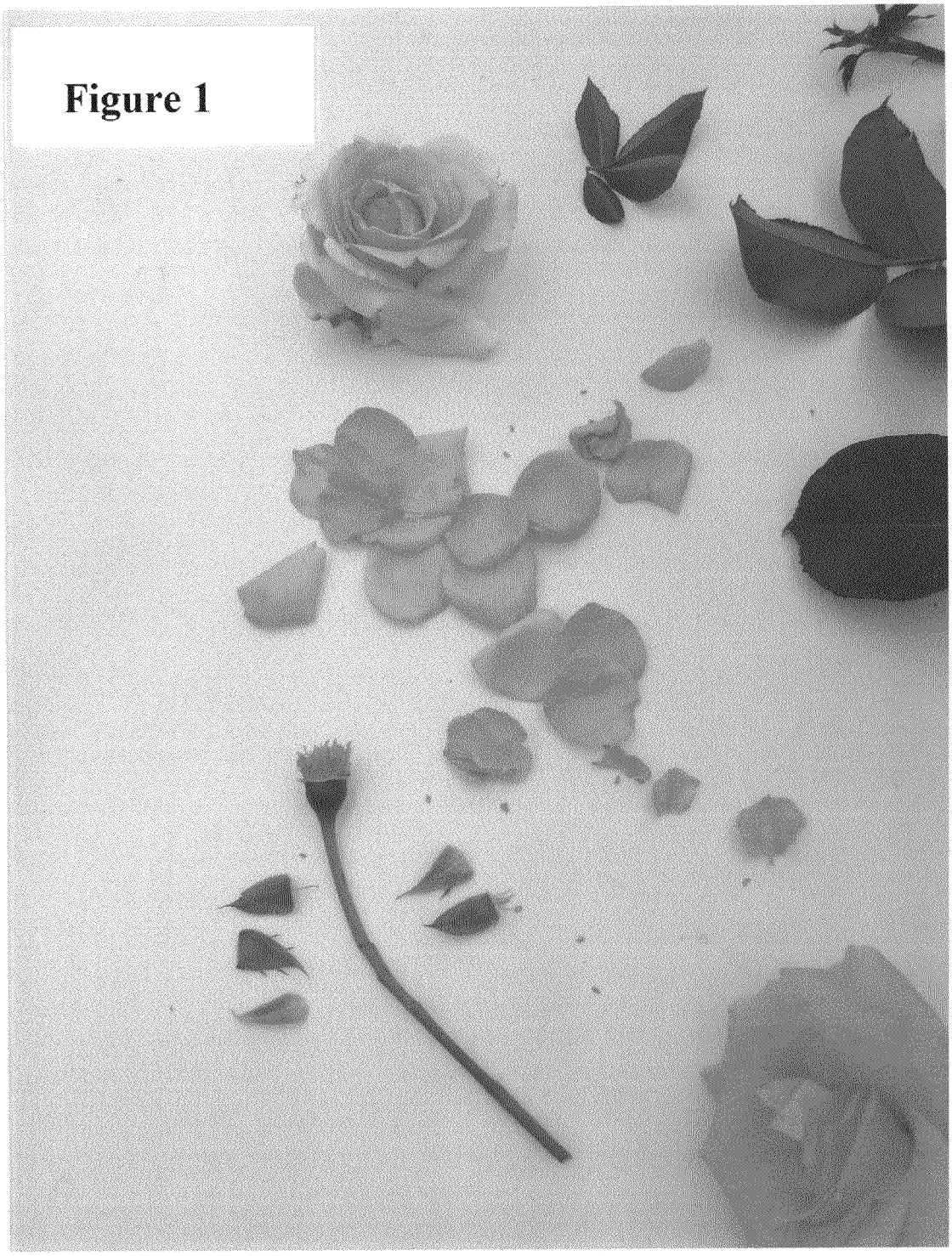
Figure 2:
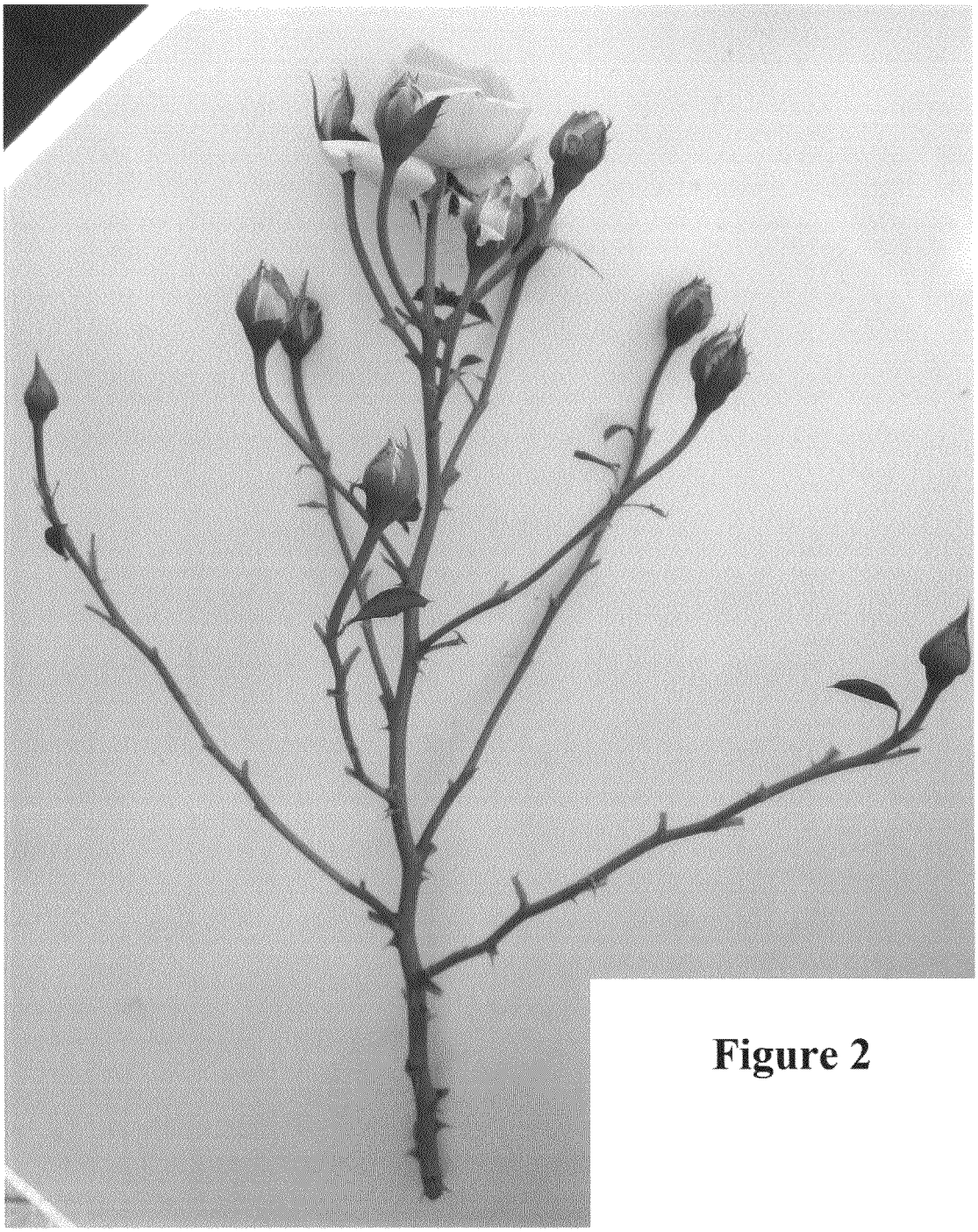

Illustrated in FIG. 2 is a flowering branch.

Figure 3:
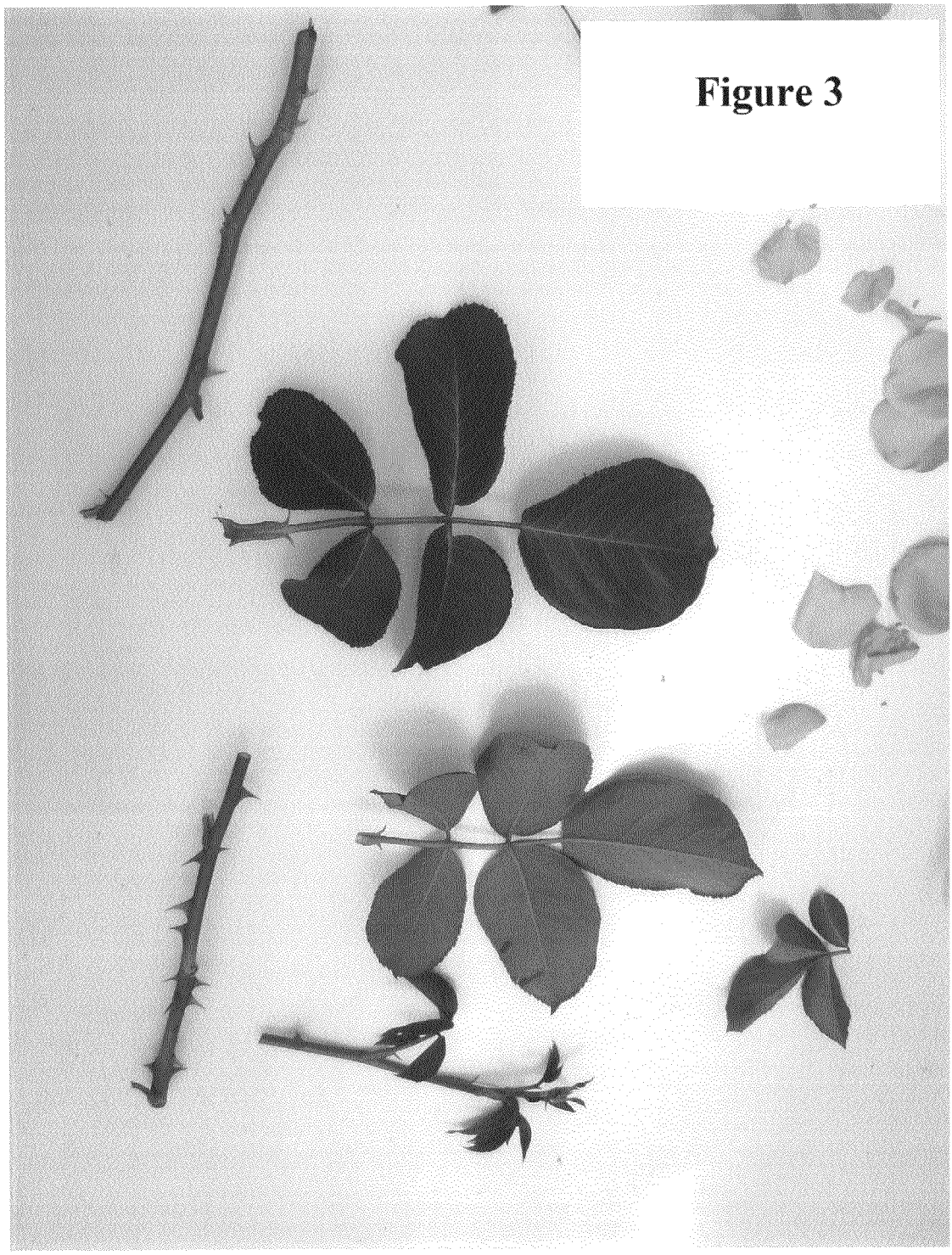

Illustrated in FIG. 3 are mature and juvenile leaves and stems.

DETAILED DESCRIPTION OF THE VARIETY

The following is a description of 'Poulpmt008', as observed in its growth in in a field nursery in Marion County, Oreg. Observed plants are 3 years of age, and were grown on *Rosa multiflora* understock. Color references are made using The Royal Horticultural Society (London, England) Colour Chart, 2001, except where common terms of color are used.

For a comparison, several physical characteristics of the rose variety 'Poulpmt005', U.S. Plant Pat. No. 18,057 are compared to 'Poulpmt008' in Chart 1.

CHART 1

| | 'Poulpmt008' | 'Poulpmt005' |
|---|---|---|
| Petal Count | 35, 4 to 5 of which are petaloids. | 33 petals total, 5 to 8 of which are petaloids |
| Flower Diameter | 80 to 90 mm | 70 mm |
| General Tonality of Flower Color | Open flowers are Yellow Group 13B blended with Yellow-Orange Group 23C. After approximately 6 days, flowers become Yellow Group 13C with intonations of Orange-Red Group 29A at the margins. | Yellow Group 4B at the periphery and Yellow Group 7C toward flower center. After the 8th day general tonality is Yellow Group 4C. |

FLOWER AND FLOWER BUD

Blooming habit: Continuous.

Flower bud:

*Size*.—Upon opening, 30 mm in length from base of receptacle to end of bud. Bud diameter is 20 mm.

*Bud form*.—Urceolate.

*Bud color*.—As sepals divide petals are Red Group 46C and Yellow Group 7C.

*Sepal inner surface*.—Color: Green Group 138C. Surface: Smooth, and moderately pubescent.

*Sepal outer surface*.—Color: Yellow-Green Group 144A with weak intonations of Greyed-Orange Group 176B. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—23 mm long by 8 mm wide.

*Receptacle*.—Texture: Smooth. Size: 10 mm in height by 12 mm wide. Color: Yellow-Green Group 144A. Shape: Funnel.

*Pedicel*.—Surface: Smooth. Length: 40 to 45 mm. Diameter: 3 to 4 mm. Color: Yellow-Green Group 144A. Strength: Strong.

*Peduncle*.—Length: 2 to 25 cm. Diameter: 4 to 5 mm. Color: Yellow-Green Group 144A.

Flower bud development: Flower buds are borne in clusters of 10 to 12 flower buds per stem, resembling a corymb.

Flower bloom:

*Fragrance*.—Moderate honey perfume scent.

*Duration*.—The blooms have a duration on the plant of approximately 10 days. Petals fall cleanly away from plant after flowers have fully matured.

*Size*.—Flower diameter is 80 to 90 mm when open. Flower depth is 35 mm.

*Flower shape*.—General shape is a high centered, double, with a high pointed center which is tightly closed.

*Shape of flower, side view*.—The upper portion is flat. The lower portion is a flattened convex.

Petalage: Under normal conditions, flowers have 35 petals total, 4 to 5 of which are petaloids.

General tonality of flower: Open flowers are Yellow Group 13B blended with Yellow-Orange Group 23C. After approximately 6 days, flowers become Yellow Group 13C with intonations of Orange-Red Group 29A at the margins.

Petal color:

*Upon opening, outer & inner petals*.—Upper surface: Yellow-Orange Group 14A blended with Yellow Group 13B. Margins have intonations of Orange Group 24C. No distinctive coloration at the petal base observed. Lower surface: Yellow-Orange Group 13B with intonations of Orange Group 24C at margins. No distinctive coloration at the petal base observed.

*After opening, outer petals*.—Upper surface: Yellow-Orange Group 14A blending with Yellow Group 13B at the margins. Additional intonations of Orange Group 24C observed on the margins. Lower surface: Yellow Group 13B becoming Yellow Group 13D at the margins. Additional splotches of Red-Purple Group N57B observed.

*After opening, inner petals*.—Upper surface: Yellow-Orange Group 17B with marginal intonations of Orange Group 26B. Lower surface: Yellow-Orange Group 13A becoming Yellow Group 13B at margins. Additional intonations of Orange Group 24C at margins.

*Basal petal spots*.—No distinctive coloration at the petal base.

Petals:

*Petal reflex*.—Moderately reflexed.

*Margin*.—Entire and uniform. Most petals have weak undulations of margin. Some inner petals and petaloids have very strong undulations.

*Shape*.—Generally rounded. Apex shape: Rounded. Base shape: Rounded.

*Size*.—40 mm (l)×43 mm (w).

*Texture*.—Smooth.

*Thickness*.—Average.

Petaloids:

*Size*.—20 mm (l) by 20 mm (w).

*Quantity*.—4 to 5.

*Shape*.—Irregular and asymmetric. The apex shape varies from acute to rounded. The base shape is acute.

*Color*.—Upper, Yellow-Orange Group 17B with marginal intonations of Orange Group 26B. Lower, Yellow-Orange Group 13A becoming Yellow Group 13B at margins. Additional intonations of Orange Group 24C at margins. No distinctive coloration at the petaloid base.

Reproductive organs:

*Pollen*.—None observed.

*Anthers*.—Size: 2.5 mm in length. Color: Yellow-Orange Group 13B. Quantity: 70 on average.

*Filaments*.—Color: Yellow Group 13A. Length: 6 mm.

*Pistils*.—Length: 4 mm. Quantity: 60 on average.

*Stigmas*.—Color: Greyed-Yellow Group 160B.

*Styles*.—Color: Orange-Red Group N34C.

*Location of stigmas*.—Inferior in location relative to the length of the filaments and the height of the anthers.

*Hips*.—None Observed.

PLANT

Plant growth: Upright. Plants are 65 cm in height, and 60 cm wide.

Stems:

*Color*.—Juvenile growth: Yellow-Green Group 144A with intonations of Greyed-Purple Group 184B. Mature growth: Yellow-Green Group 144A.

*Length*.—On average, canes are 40 cm from the base of the plant to the flowering portion.

*Diameter*.—5 mm.

*Internodes*.—On mature canes, there is an average distance of 45 mm between nodes.

*Surface texture*.—Young wood: Smooth. Older wood: Smooth.

Long prickles:

*Incidence*.—5 prickles per 10 cm of stem.

*Size*.—Average length of prickles on mature stems is 7 mm.

*Shape*.—Upper portion is linear. Lower portion is deep concave.

*Color*.—Juvenile prickles: Greyed-Red Group 178A. Mature prickles: Greyed-Yellow Group 161B.

Plant foliage:

*Compound leaf*.—140 mm (l)×120 (w).

*Quantity*.—2 leaves per 10 cm of stem on average.

*Leaf bearing angle to the stem*.—45 degrees.

*Color of juvenile foliage*.—Upper and lower side: Greyed-Purple Group 183B.

*Color of mature foliage*.—Upper side: Yellow-Green Group 147A. Lower side: Yellow-Green Group 146B.

Plant leaves and leaflets:

*Stipules*.—Size: 25 mm in length and 8 mm in width. Quantity: 2 per compound leaf. Shape: Linear, slightly broad based with outward extending apices. Margins: Finely serrated. Color: Yellow-Green Group 146B.

*Petiole*.—Length: 35 mm. Diameter: 2 mm.

*Upper surface*.—Color: Yellow-Green Group 144A.

*Lower surface*.—Color: Yellow-Green Group 144B.

*Rachis*.—Length: 45 mm. Upper surface: Yellow-Green Group 144A. Lower surface: Yellow-Green Group 144B.

*Leaflet*.—Quantity: Normal number of leaflets per leaf in the middle of the stem is 5 leaflets. Margins: Doubly serrated. Size: Average size of the terminal leaflet on normal leaves is 70 mm in length by 50 mm wide. Shape: Generally oval. Base: Rounded. Apex: Cuspidate. Texture: Smooth. Thickness: Average. Arrangement: Odd pinnate. Venation: Reticulate. Glossiness: Very glossy.

Disease resistance: Above average resistance to powdery and downy mildew, rust, black spot, and *Botrytis* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the Hybrid Tea rose class named 'Poulpmt008', substantially as illustrated and described herein, due to its abundant yellow-orange flowers, disease resistance, and extended period of bloom.

* * * * *